(12) United States Patent
Hunter-Jones et al.

(10) Patent No.: US 11,259,741 B2
(45) Date of Patent: Mar. 1, 2022

(54) SKIN ELASTICITY MEASUREMENT

(71) Applicants: Nicholas Hunter-Jones, Lincoln, MA (US); Alexander Isakov, Sudbury, MA (US)

(72) Inventors: Nicholas Hunter-Jones, Lincoln, MA (US); Alexander Isakov, Sudbury, MA (US)

(*) Notice: Subject to any disclaimer, the term of this patent is extended or adjusted under 35 U.S.C. 154(b) by 782 days.

(21) Appl. No.: 16/026,813

(22) Filed: Jul. 3, 2018

(65) Prior Publication Data
US 2018/0310871 A1 Nov. 1, 2018

Related U.S. Application Data

(62) Division of application No. 13/461,355, filed on May 1, 2012, now Pat. No. 10,123,733, which is a division of application No. 11/736,954, filed on Apr. 18, 2007, now Pat. No. 8,175,689.

(60) Provisional application No. 60/895,588, filed on Mar. 19, 2007.

(51) Int. Cl.
*A61B 5/00* (2006.01)
(52) U.S. Cl.
CPC ............ *A61B 5/442* (2013.01); *A61B 5/0055* (2013.01); *A61B 5/4875* (2013.01); *A61B 5/68* (2013.01)
(58) Field of Classification Search
CPC .......... A61B 5/0055; A61B 5/441–442; A61B 5/4875; A61B 5/68
See application file for complete search history.

(56) References Cited

U.S. PATENT DOCUMENTS

| | | |
|---|---|---|
| 3,781,116 A | 12/1973 | Jones |
| 3,866,246 A | 2/1975 | Seamone |
| 4,206,769 A | 6/1980 | Dikstein |
| 4,259,965 A | 4/1981 | Fukuda |
| 4,586,515 A | 5/1986 | Berger |
| 4,765,345 A | 8/1988 | Adib |
| 4,771,237 A | 9/1988 | Daley |
| 4,947,851 A | 8/1990 | Sarvazyan et al. |
| 4,976,272 A * | 12/1990 | Bazin ........................ G01N 3/00 600/587 |
| 5,005,975 A | 4/1991 | Kawai et al. |
| 5,054,502 A | 10/1991 | Courage |
| 5,480,454 A | 1/1996 | Bozeman |
| 5,826,578 A | 10/1998 | Curchod |
| 6,016,439 A | 1/2000 | Acker |

(Continued)

FOREIGN PATENT DOCUMENTS

EP 0255809 * 10/1988
WO WO 2006/021808 3/2006

OTHER PUBLICATIONS

Laron, "Skin Turgor as a Quantitative Index of Dehydration in Children", Pediatrics, 19:816-822, 1957.

(Continued)

*Primary Examiner* — Amelie R Davis
(74) *Attorney, Agent, or Firm* — Fish & Richardson P.C.

(57) ABSTRACT

A method of measuring a characteristic of a skin, including varying an air pressure in a chamber positioned adjacent to a skin, in which the chamber has an opening that exposes the skin to changes in the air pressure in the chamber. A plurality of measurements of surface profiles of the skin are made over a period of time as the surface profile of the skin varies in response to changes in the air pressure.

31 Claims, 6 Drawing Sheets

(56) References Cited

U.S. PATENT DOCUMENTS

| | | | |
|---|---|---|---|
| 6,017,316 | A | 1/2000 | Ritchart |
| 6,285,958 | B1 | 9/2001 | Wolf et al. |
| 6,302,856 | B1 | 10/2001 | Golhofer |
| 6,324,419 | B1 | 11/2001 | Guzelsu et al. |
| 6,615,064 | B1 | 9/2003 | Aldrich |
| 6,619,423 | B2 | 9/2003 | Courage |
| 7,344,498 | B1 | 3/2008 | Doughty et al. |
| 7,862,522 | B1 | 1/2011 | Barclay |
| 2001/0003802 | A1 | 6/2001 | Vitale |
| 2002/0173799 | A1 | 11/2002 | Besharim |
| 2002/0198472 | A1 | 12/2002 | Kramer |
| 2003/0060927 | A1 | 3/2003 | Gerbi |
| 2004/0199058 | A1 | 10/2004 | Karam et al. |
| 2005/0166687 | A1 | 8/2005 | Kaneko et al. |
| 2006/0082590 | A1 | 4/2006 | Stevick et al. |
| 2006/0241459 | A1 | 10/2006 | Tai |
| 2007/0165213 | A1 | 7/2007 | Fang et al. |
| 2010/0179440 | A1 | 7/2010 | Lee |

OTHER PUBLICATIONS

Draaijers, et al., "Skin Elasticity Meter or Subjective Evaluation in Scars: A Reliability Assessment", Burns, vol. 30, Issue 2, pp. 109-114, Mar. 2004.

Dobrev, H.P., Folia Med (Plovdiv). 2002; 44(3):5-10.

Dobrev. "Use of Cutometer to assess epidermal hydration." Skin Res Technol. Nov. 2000; 6(4):239-244; abstract.

* cited by examiner

SKIN ELASTICITY MEASUREMENT

CLAIM OF PRIORITY

This application is a divisional and claims the benefit of U.S. patent application Ser. No. 13/461,355, filed on May 1, 2012, which is a divisional and claims the benefit of U.S. patent application Ser. No. 11/736,954, filed on Apr. 8, 2007, which claims the benefit of U.S. Provisional Application Ser. No. 60/895,588, filed on Mar. 19, 2007. The above applications entire contents are hereby incorporated by reference.

BACKGROUND

This invention relates to skin elasticity measurement.

Mechanical properties of skin (e.g., elasticity of skin) may change due to, e.g., disease, stress, or dehydration. When the body becomes dehydrated as a result of diseases (e.g., ones that cause diarrhea) or reduced liquid intake (e.g., famine or marathon running), the skin becomes "doughy" and does not snap back when pinched. A fluid loss of 5% of the body weight is considered mild dehydration. A 10% loss is regarded as moderate dehydration, and 15% or more fluid loss is severe dehydration. For example, in a test for dehydration called the "pinch test" or "turgor test," the skin is grasped and pulled up in a pinch-like manner and then release. Healthy skin will quickly snap back to its undeformed state, whereas dehydrated skin slowly returns to its undeformed state.

SUMMARY

In one aspect, in general, a method of measuring a characteristic of a skin, the method including varying an air pressure in a chamber positioned adjacent to a skin, the chamber having an opening that exposes the skin to changes in the air pressure in the chamber, making a plurality of measurements of surface profiles of the skin over a period of time as the surface profile of the skin varies in response to changes in the air pressure, and outputting the measurements or a value derived from the measurements.

Implementations of the method may include one or more of the following features. Measuring the surface profiles of the skin includes using a video camera to capture images of the surface profiles of the skin as the skin rises or falls in response to changes in the air pressure. The method includes providing an indication of a likelihood of dehydration of a person or an animal based on measurements of the surface profile of the skin. The method includes forming an air-tight coupling between the skin and a rim surrounding the opening.

In another aspect, in general, a method includes varying an air pressure in a chamber positioned adjacent to a skin, the chamber having an opening that exposes the skin to changes in the air pressure in the chamber; making a plurality of measurements of a level of a surface of the skin over a period of time as the surface of the skin rises or falls in response to changes in the air pressure in the chamber; and using the plurality of measurements to determine an elasticity of the skin.

Implementations of the method may include one or more of the following features. Measuring the level of the surface of the skin includes using a linear potential meter to measure the level of the surface of the skin. Measuring the level of the surface of the skin includes using a Hall sensor to measure a magnetic field generated by a magnet attached to the surface of the skin.

In another aspect, in general, a method includes varying an air pressure in a first chamber positioned adjacent to a skin, the first chamber defining an opening that exposes the skin to changes in the air pressure in the chamber, making a plurality of measurements of a volume of the skin in the first chamber over a period of time as the volume of the skin in the first chamber changes in response to changes in the air pressure in the first chamber, and outputting the measurements or a value derived from the measurements.

Implementations of the method may include one or more of the following features. The method includes varying a volume of a second chamber that is coupled to the first chamber to cause the air pressure in both the first and second chambers to vary over the period of time. Making a plurality of measurements of a volume of the skin in the first chamber includes making a plurality of measurements of the air pressure in the first and second chambers over the period of time as the air pressure changes in response to the variations in the volume of the second chamber, and determining the volume of the skin in the first chamber based on the measurements of the air pressure.

An apparatus for measuring a characteristic of a skin, the apparatus includes a chamber to be positioned adjacent to a skin, the chamber having an opening that exposes the skin to changes in an air pressure in the chamber; a pump to vary the air pressure in the chamber; and a video camera to capture images of surface profiles of the skin in the chamber over a period of time as the surface profile of the skin changes in response to changes in the air pressure in the chamber.

Implementations of the apparatus may include one or more of the following features. The apparatus includes a controller to control the pump and the video camera to capture images of surface profiles of the skin over a period of time. The apparatus includes a data processor to process captured image data and provide an indication of a likelihood of dehydration of a body based on a result of the processing of the image data. The chamber has an inner surface having a dark color to enhance a contrast between the skin and the inner surface of the chamber. The apparatus includes a vent valve to provide a passage between the chamber at the atmosphere. The chamber includes a cuvette.

An apparatus for measuring a characteristic of a skin, the apparatus includes a chamber to be positioned adjacent to a skin, the chamber defining an opening that exposes the skin to changes in an air pressure in the chamber; a pump to vary the air pressure in the chamber; and a sensor to measure a level of a surface of the skin in the chamber over a period of time as the surface of the skin in the chamber rises or falls in response to changes in the air pressure in the chamber.

Implementations of the apparatus may include one or more of the following features. The sensor includes a linear potential meter to measure the level of the surface of the skin. The sensor includes a Hall sensor to measure a magnetic field generated by a magnet attached to the surface of the skin.

An apparatus for measuring a characteristic of a skin, the apparatus includes a first chamber to be positioned adjacent to a skin, the first chamber defining an opening that exposes the skin to changes in an air pressure in the first chamber; a second chamber having an adjustable volume and being coupled to the first chamber, the first and second chambers having a common air pressure; a pump to reduce an air pressure in the first and second chambers; a pressure sensor to sense the air pressure; and a data processor to determine a change in a volume of the skin in the first chamber based on measurements of the air pressure by the pressure sensor.

Implementations of the apparatus may include one or more of the following features. The second chamber includes a motor and a syringe, the motor to drive a plunger of the syringe to change the volume in the second chamber.

The apparatuses and methods can have one or more of the following advantages. The elasticity of a skin can be quickly measured, and information about skin elasticity can be used as a factor in evaluating whether a person or animal is dehydrated. The device for measuring skin elasticity is low cost, small, convenient to carry.

Other features and advantages of the invention are apparent from the following description, and from the claims.

DESCRIPTION

Mechanical properties of skin, such as elasticity of the skin, can be measured by applying a force to the skin and measuring how the skin responds to the force. For example, a suction force can be applied to pull the skin, and sensors can be used to measure the skin while the suction force is applied and/or after the suction force is removed. In some examples, a sensor may be used to determine the amount of time it takes for the skin to deform a certain amount when a given suction force is applied. In some examples, a sensor may be used to measure the profile of the skin over time as the skin returns its original state after the suction force is removed.

Figure 1:
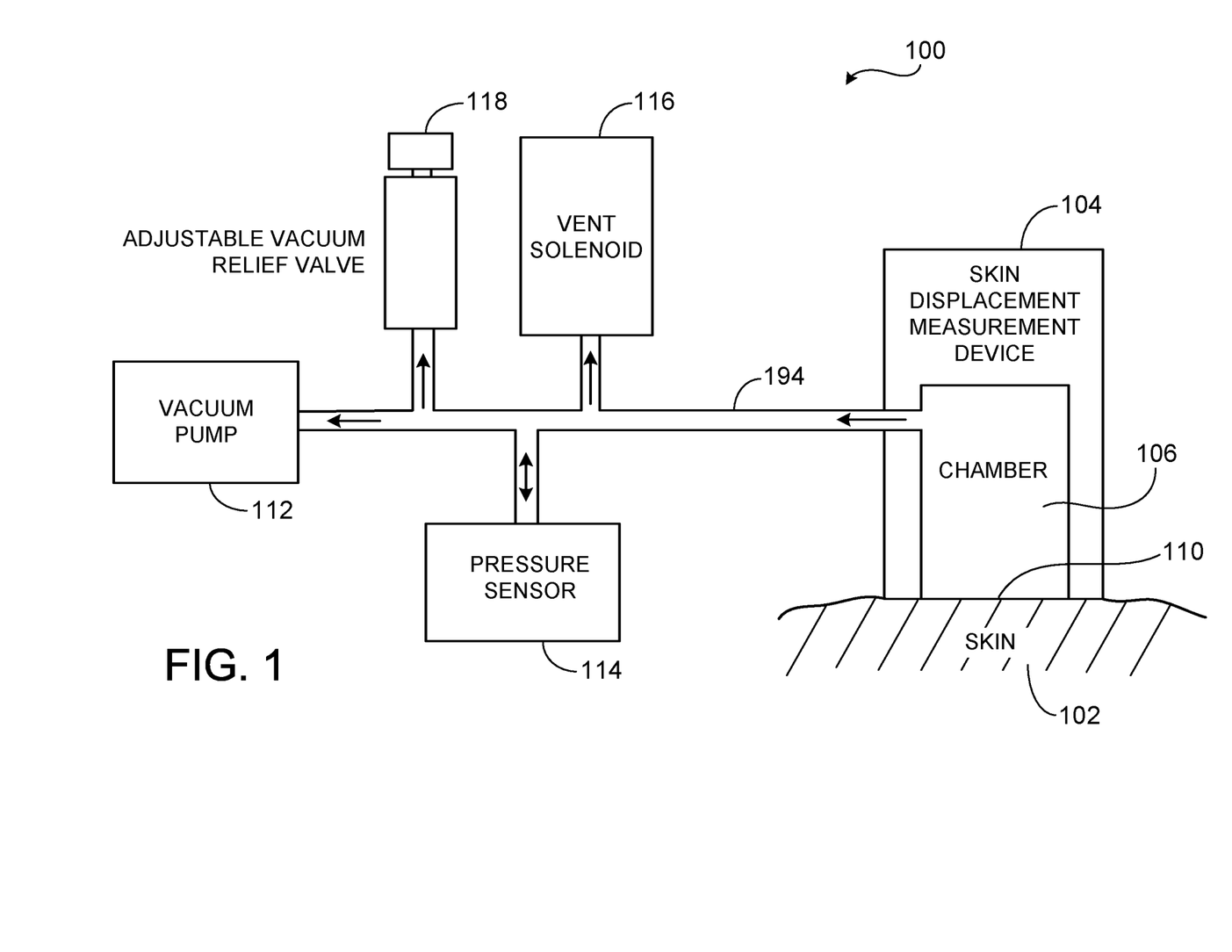
FIG. 1 is a schematic diagram of a skin measurement system.

FIG. 1 is a schematic diagram of a skin measuring system 100 for measuring mechanical properties of a skin 102. the mechanical properties may include, e.g., an elasticity of the skin 102. The system 100 includes skin displacement measuring device 104 that measures positions of the skin 102 as a suction force pulls on the skin 102 over a period of time. The device 104 includes a chamber 106, which may be a cuvette, that is placed over the skin 102. The device 104 is pressed against the skin 102 so that the skin 102 completely covers an opening 110 of the chamber 106, preventing air from entering or leaving the chamber 106 through the opening 110. The chamber 106 is coupled to a vacuum pump 112 through a tube 194. As the vacuum pump 112 operates to reduce the air pressure in the chamber 106, a suction force is generated on the skin 102, pulling the skin 102 upwards into the chamber 106.

The system 100 includes a pressure sensor 114, a vent solenoid 116, and an adjustable vacuum relief valve 118 that are coupled to the tube 194. The level of vacuum in the chamber 106 can be adjusted by adjusting vacuum relief valve 118 to control the amount of air entering the tube 194 through the valve 118. The vent solenoid 116 when activated provides a passage between the tube 194 and the outside environment so that the pressure in the chamber 106 can quickly return to atmospheric pressure.

The description below includes examples of skin elasticity measurement systems that use different methods for measuring the displacement of the skin 102.

Example 1

Figure 2:
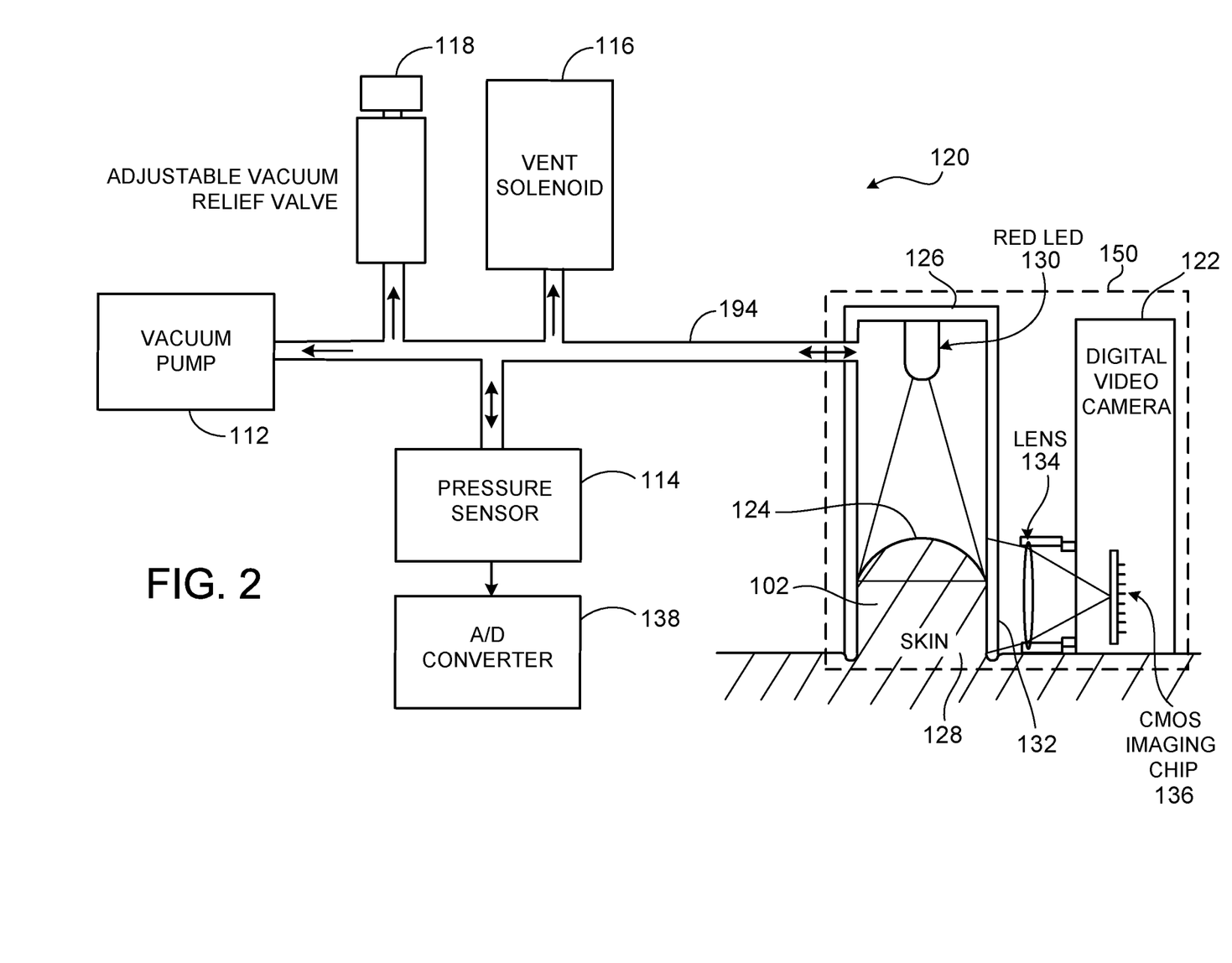
FIG. 2 is a schematic diagram of a skin measuring system.

FIG. 2 is a schematic diagram of an example of a skin measuring system 120 for measuring mechanical properties of a skin 102. The system 120 has a skin displacement measuring device 150 that includes a digital video camera 122 for capturing images of the skin surface profile 124 over a period of time. The system 120 includes a cuvette 126 that is pressed against the skin 102 during measurement. The cuvette 126 can have, e.g., a 10 mm×10 mm square cross section. The cuvette 126 has an opening 128 through which the skin 102 is partially pulled into the cuvette 126 in response to a reduction in the air pressure in the cuvette 126. The system 120 includes a vacuum pump 112, a pressure sensor 114, a vent solenoid 116, and an adjustable vacuum relief valve 118, similar to those shown in FIG. 1.

A light source, e.g., a red light emitting diode (LED) 130, illuminates the skin 102 in the cuvette 126. To provide a constant illumination, the LED 130 can be driven by, e.g., a 5 V voltage regulator connected to a 9 V battery. A resistor (not shown) in series with the LED 130 can be used to limit the current flowing through the LED 130 to, e.g., about 10 mA to allow the LED 130 to provide adequate illumination.

The cuvette 126 can be made of, e.g., clear plastic. Both the inside and outside of the cuvette 126 are painted, e.g., matte black, except for a window 132 on a sidewall of the cuvette 126 near the opening 128. Painting the inside and outside of the cuvette 126 matte black prevents reflections on the interior and exterior surfaces of the cuvette 126 so that clear images of the skin can be captured by the digital video camera 122. The matte black wall of the cuvette 126 provides a dark background in contrast to the skin 102 illuminated by the red LED 130.

The digital video camera 122 includes a lens 134 and an image sensor 136, e.g., a CMOS sensor. The lens 134 is placed adjacent to the window 132 and focuses light reflected from the skin 102 in the cuvette 126 onto the image sensor 136. This allows the digital video camera 122 to capture images of the surface profile of the skin 102 as the skin 102 rises or falls in the cuvette 126 in response to changes in the air pressure in the cuvette 126.

The system 120 can be used to make at least two types of measurements. In a first type of measurement, the profile of the skin 102 is measured without correlating the profile to the air pressure in the cuvette 126. The measurement can be performed when the air pressure in the cuvette 126 is decreasing or increasing.

For example, the vacuum pump 112 can be activated to start pumping air out of the cuvette 126, and images from the digital video camera 122 can be used to determine changes in the skin profile over a period of time. The suction force generated by the vacuum pump 112 is substantially constant. The amount of pressure change (from the preset pressure to the atmospheric pressure) is substantially constant, assuming that the atmospheric pressure is substantially constant. The amount of time for the skin 102 to reach a certain height, the height reached by the skin 102 after a certain amount of time, or the profile of the skin 102 after a certain amount of time, provides information about the elasticity of the skin 102. This information may be useful in determining general conditions or healthiness of the skin 102.

The system 100 can measure how the skin profile changes over time as the air pressure in the cuvette 126 abruptly increases from a preset low-pressure level to the atmospheric pressure. When the vacuum pump 112 pumps air out of the cuvette 126 and the air pressure reduces to the preset low-pressure level, the vent solenoid 116 can be activated to allow air to enter the tube 122, causing the air pressure in the cuvette 126 to abruptly increase to the atmospheric pressure. Changes of the skin profile after the vent solenoid 116 is activated can be measured using images captured by the digital video camera 122.

The amount of pressure change (from the preset pressure to the atmospheric pressure) is substantially constant, assuming that the atmospheric pressure is substantially constant. The amount of time for the skin 102 to return to its original state, the amount of change in the height of the skin surface after a certain amount of time, or the amount of change in the profile of the skin 102 after a certain amount of time, provides information about the elasticity of the skin 102. This information may be useful in determining general conditions or healthiness of the skin 102. The original state of the skin refers to the state of the skin 102 under normal atmospheric pressure.

The skins of a healthy person and a dehydrated person may show different skin profile versus time characteristics. For example, when the vent solenoid 116 is activated to cause the air pressure in the cuvette 126 to abruptly increase from a preset low-pressure level to the atmospheric pressure, the skin of a healthy person may quickly return to its original state, whereas the skin of a dehydrated person may take a longer amount of time to return to its original state.

A database can be established to indicate, for example, for a certain age and gender, when the amount of time required for the skin to return to its original state is beyond a certain threshold level, there is a higher likelihood that the person is dehydrated.

In a second type of measurement, the profile of the skin 102 is measured and correlated with the air pressure in the cuvette 126. For example, the vacuum pump 112 can be activated to gradually reduce the air pressure in the cuvette 126. At the same time, the pressure sensor 114 senses the air pressure, and the digital video camera 122 captures images of the skin profile over a period of time. The images from the camera 122 can be processed to determine how the skin profile changes in response to changes in the air pressure in the cuvette 126. The change in the skin profile in response to changes in the air pressure in the cuvette 126 can provide information about the elasticity of the skin 102. This information may be useful in determining the general conditions or healthiness of the skin 102.

In one version of the system 120, the output of the pressure sensor 114 is sent to an analog-to-digital converter (ADC) 138. The outputs of the ADC 138 and the digital video camera 122 are sent to a notebook computer (not shown) (or a personal digital assistant, PDA) wirelessly or through, e.g., a Universal Serial Bus (USB) cable. The computer (or PDA) executes an application program that processes the measurement data from the pressure sensor 114 and the images from the digital video camera 122.

The application program may generate a number of characteristics that can be used as one of the factors in evaluating the healthiness or conditions of the skin 102. The images captured by the digital video camera 122 include red portions with black backgrounds. The red portions represent the skin 102 inside the cuvette 126 illuminated by the red LED 130. The application program may identify the highest point of the red portion in each image to determine how high the skin 102 rises in the cuvette 126 over time in response to a change in the air pressure.

The application program may count the number of pixels in the red region to determine the area of the red region, which provides an indication of the volume of the skin in the cuvette 126. The application program may perform integration to estimate the volume of the skin 102 in the cuvette 126. The application program may correlate the changes in the skin profile to changes in the air pressure in the cuvette 126.

The system 120 may include a controller (not shown) to control some of the processes described above. For example, the user may press the cuvette 126 against a person's skin and press a button (not shown) of the system 120 to start a measurement sequence. Pressing the button generates a control signal that triggers the controller to activate the pump 112 to start pumping. The pressure sensor 114 senses the air pressure in the cuvette 126. The output from the pressure sensor 114 is monitored by the application program. When the air pressure reaches a preset low-pressure level, the controller activates the vent solenoid 116 to cause the air pressure to return to atmospheric pressure, and deactivates the pressure pump 112. The application program processes the measurement data from the pressure sensor 114 and the digital video camera 122, and compares the measured data with pre-established data in a database. Base on the comparison, the application program outputs information on a display (not shown), in which the information can be used as one of the factors in evaluating the general conditions or healthiness of the skin 102.

The system 120 can be built using off-the-shelf components. For example, the digital video camera 122 can be, e.g., a WebCam !Live Ultra video camera, available from Creative Labs, Inc., Milpitas, Calif. The vacuum pump 112 can be a model 8018Gt 24 V diaphragm vacuum pump, available from Namiki Precision of California Inc., Belmont, Calif. The pressure sensor 114 can be, e.g., a gas pressure sensor model GPS-BTA, available from Vernier Software and Technology, Beaverton, Oreg. The computer software for processing the data from the pressure sensor 114 can be, e.g., LoggerPro, also available from Vernier Software and Technology. The LoggerPro software automatically detects the gas pressure sensor characteristics and records the output from the pressure sensor 114 directly in metric pressure units (i.e., Pa). The LoggerPro software can be set to record the pressure at, e.g., 200 samples per second while the vacuum pump 112 lowers the air pressure in the cuvette 126.

In another version of the system 120, a built-in data processor processes the data from the pressure sensor 114 and the images from the digital video camera 122. The system 120 may include a small liquid crystal display to show the measurement results. For example, the system 120 may show the number of seconds that it takes from the skin 102 to return to its original state when the air pressure changes abruptly from a preset low-pressure level to the atmospheric pressure. The user may consult a handbook that include tables of statistical information on skin measurements for people of different ages and gender to determine whether there is a likelihood that the person being measured is dehydrated. In some examples, the system 120 may have a flash memory that stores a database that includes statistical information on skin measurements for people of different ages and gender. Based on a comparison of the measurements and the statistical values in the database, the system 120 may provide an output on the display showing whether there is a likelihood that the person being measured is dehydrated.

Figure 3:
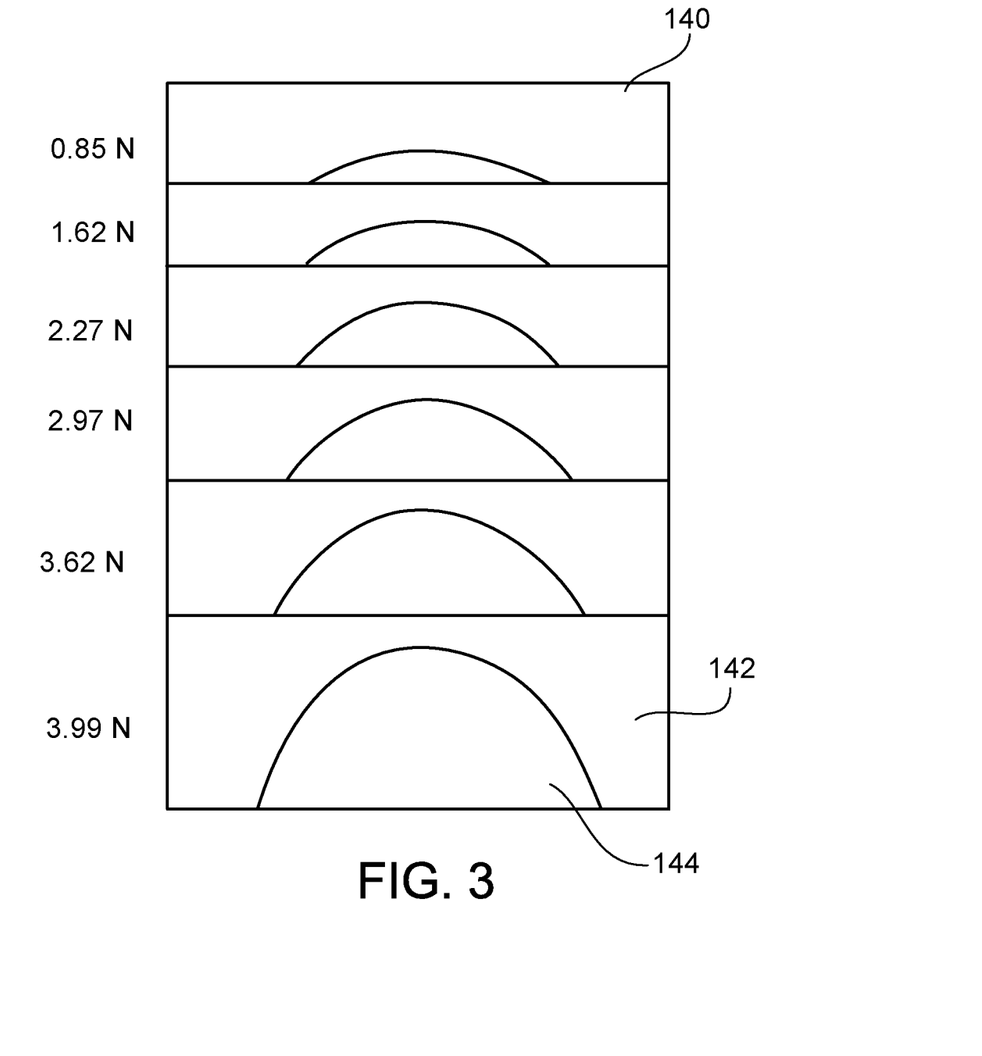
FIG. 3 show images of skin surface profiles.

FIG. 3 show examples of images 140 of the surface profile of the skin 102 captured by the digital video camera 122. The images 140 were obtained using simulation. The darker region 142 represents the matt black surface of the cuvette 122, and the lighter region 144 represents the skin 102 inside the cuvette 122 illuminated by the red LED 130. As the air pressure in the cuvette 122 decreases, the suction force on the skin 102 increases and a larger portion of the skin 102 is pulled into the cuvette 122.

Example 2

Figure 4:
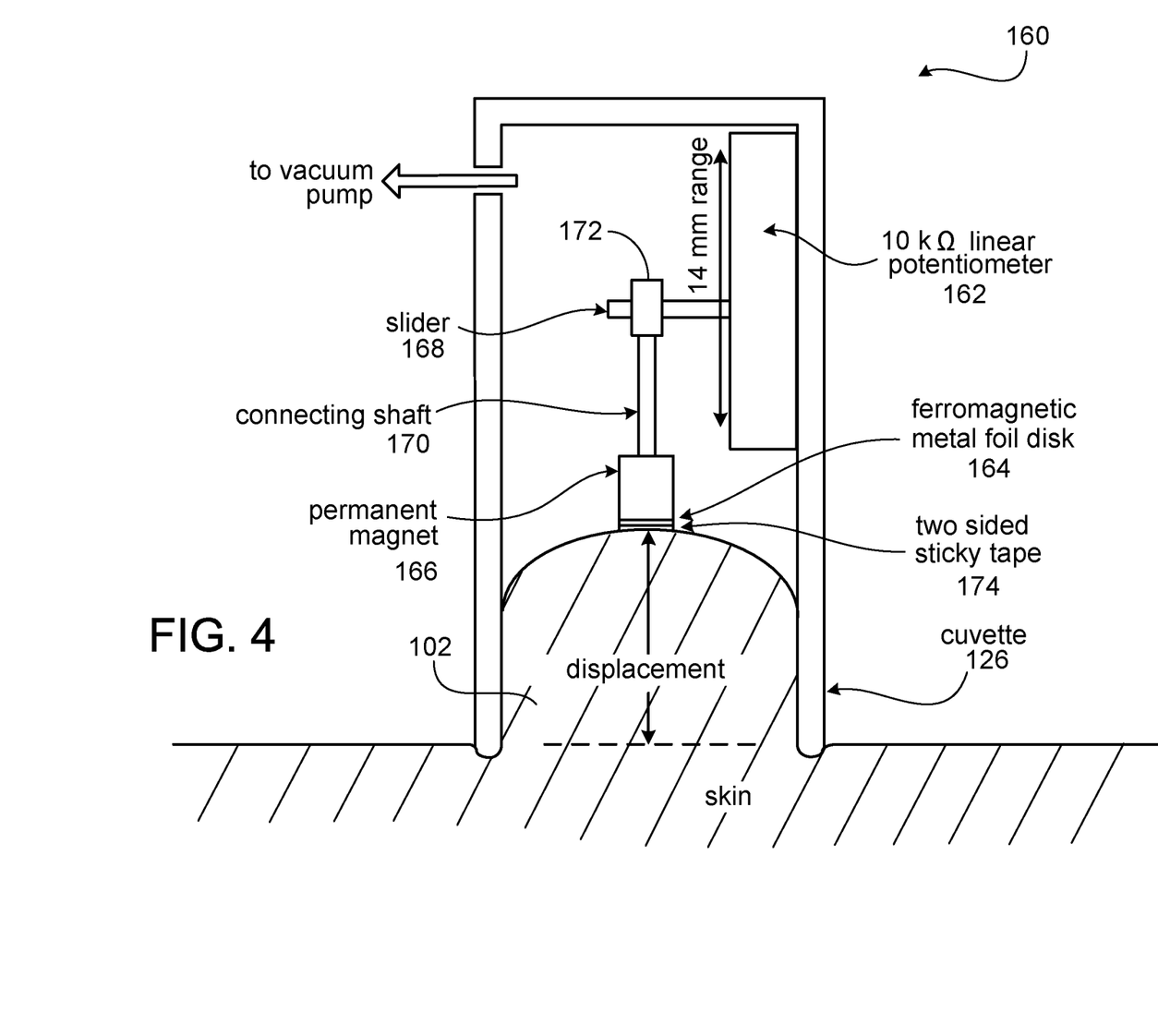
FIG. 4 is a schematic diagram of a skin displacement measuring device.

FIG. 4 is a schematic diagram of an example of a skin displacement measuring device 160 that includes a linear potentiometer 162 placed inside a cuvette 126. The device 160 can be used in the system 120 of FIG. 2 to replace to device 150. A ferromagnetic metal foil disk 164 is attached to a region of the skin 102 being measured for displacement. The disk 164 can be attached to the skin 102 in numerous ways, such as using a two sided sticky tape 174. As the skin 102 rises or falls in the cuvette 126, the disk 164 rises or falls correspondingly. The linear potentiometer 162 measures the displacement of the disk 164, indirectly measuring the displacement of the skin 102.

The linear potentiometer 162 uses an operating voltage that is provided by a 5V voltage regulator chip (not shown) connected to a 9 V battery (not shown). The linear potentiometer 162 has a slider 168, in which different positions of the slider 168 correspond to different voltage outputs of the potentiometer 162. A permanent magnet 166 is coupled to a connecting shaft 170, which is coupled to the slider 168. The magnet 166 is magnetically coupled to the foil disk 164. As the disk 164 rises or falls, the slider 168 moves in response, changing the voltage output of the potentiometer 162.

When the vacuum pump 112 pumps air out of the cuvette 126, the skin 102 rises or falls depending on the pressure inside the cuvette 126. The displacement of the skin is measured by the linear potentiometer 106. For example, when the skin 102 rises, the slider 168 is pushed upwards so that the potentiometer 162 outputs a higher voltage signal. Conversely, when the skin 102 falls, the slider 168 is pulled downwards so that the potentiometer 162 outputs a lower voltage signal. The output voltage can be recorded as a function of time, allowing the skin displacement to be measured as a function of time.

Instead of using the output voltage of the potentiometer 162 as an indication of the position of the slider 168, a ruler (not shown) may be placed behind the slider 168, so that the position of the slider 168 can be determined based on the ruler.

Using the potentiometer 162, it is possible to determine the amount of time for the skin 102 to reach a certain height, or the height reached by the skin 102 after a certain amount of time. This information can be used to determine the elasticity of the skin 102, which may be used as a factor in determining general conditions or healthiness of the skin 102.

The linear potentiometer 162 can be, e.g., an Alps model RDC1014A09, with a travel distance of 14 mm, an operating force of 250 mN, and a total resistance of 10 kΩ The magnet 166 can be, e.g., a cylindrical, miniature, high energy density NdFeB permanent magnet. The foil disc 164 can be, e.g., cut from feeler-gage stock. The 5V voltage regulator chip can be, e.g., from ST Microelectronics.

Example 3

Figure 5:
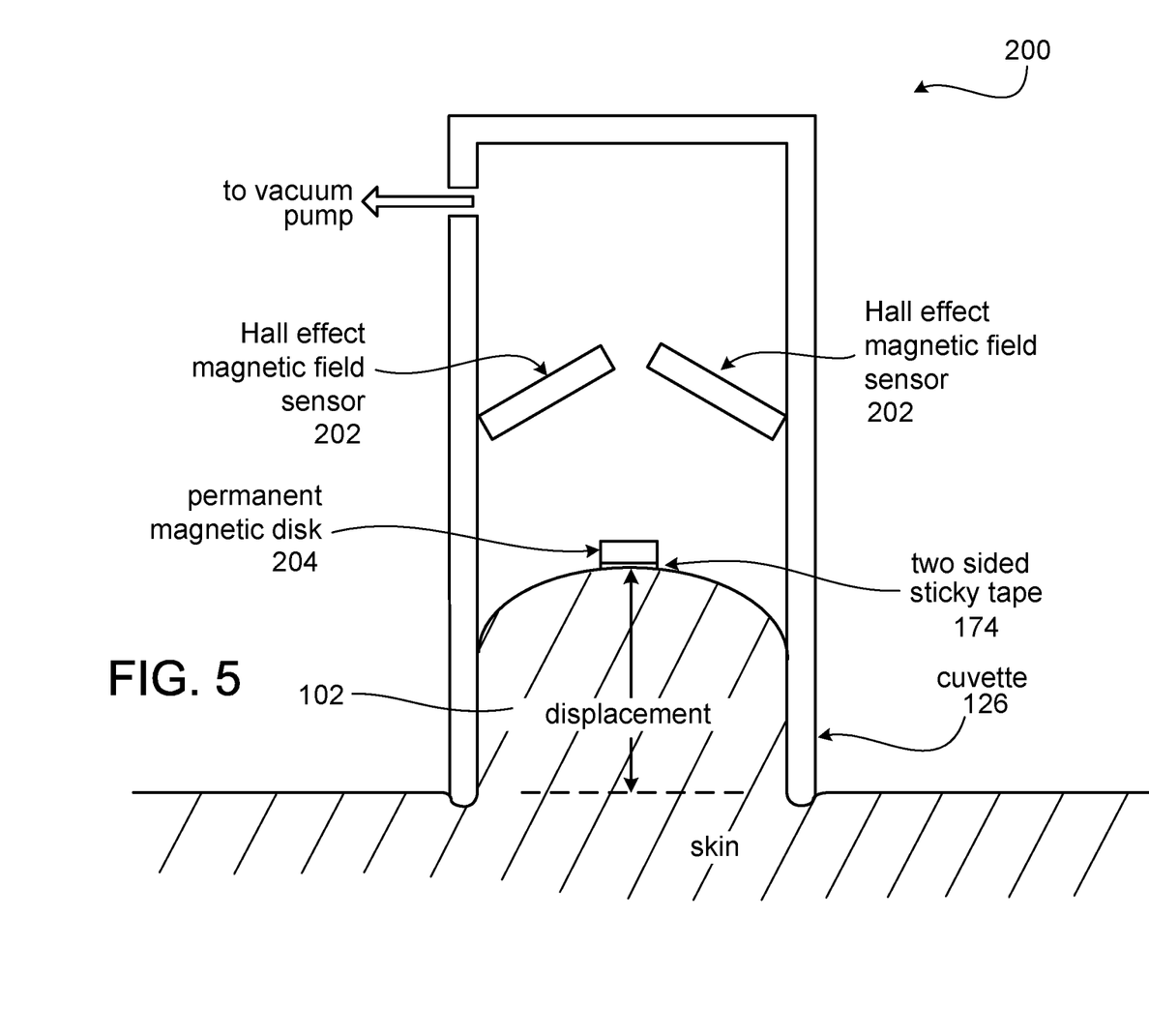
FIG. 5 is a schematic diagram of a skin displacement measuring device.

FIG. 5 is a schematic diagram of an example of a skin displacement measuring device 200 that includes a cuvette 126 for forming a chamber over a portion of a skin 102 to be measured, and two Hall effect magnetic field sensors 202 (referred to as Hall-effect sensors 202) for measuring displacement of a permanent magnetic disk 204 attached to the skin 102. The Hall-effect sensors 202 can be placed inside or outside of the cuvette 126. When the magnetic disk 204 rises or falls in response to changes in the air pressure in the cuvette 126, the magnetic field generated by the magnetic disk 204 changes. This change in the magnetic field is measured by the Hall-effect sensors 202. In some examples, in order to reduce the effect of tilting of the magnetic disk 204 as the disk 204 moves with the skin 102, the two Hall-effect sensors 202 can be mounted orthogonal to each other in the cuvette 126.

The Hall-effect sensors 202 can be, e.g., model 1321 from Allegro Microsystems. The precision digital micrometer can be, e.g., a micrometer available from Mitutoyo America Corporation, Aurora, Ill. The magnetic disk 204 can be, e.g., made of NdFeB and have a diameter of 3 mm and a thickness of 1 mm.

The output of the Hall sensors 202 can be calibrated using a precision digital micrometer. For example, during a calibration process, the micrometer measures the displacement of the skin 102 at the same time that the Hall sensors 202 measure the changes in the magnetic field due to changes in the positions of the magnetic disk 204. A calibration table can be established to correlate the output of the Hall sensor 202 to a corresponding skin displacement. Later, the micrometer can be removed, and displacement of the skin 102 can be measured using the Hall sensors 202 and the calibration table.

In order to reduce the effect of the magnet 106 tilting as it moves with the skin, the two Hall sensors may be mounted orthogonal to each other on the chamber 104 or cuvette. A chamber 104 with sloping sides may assist in the placement of the sensors.

Example 4

Figure 6:
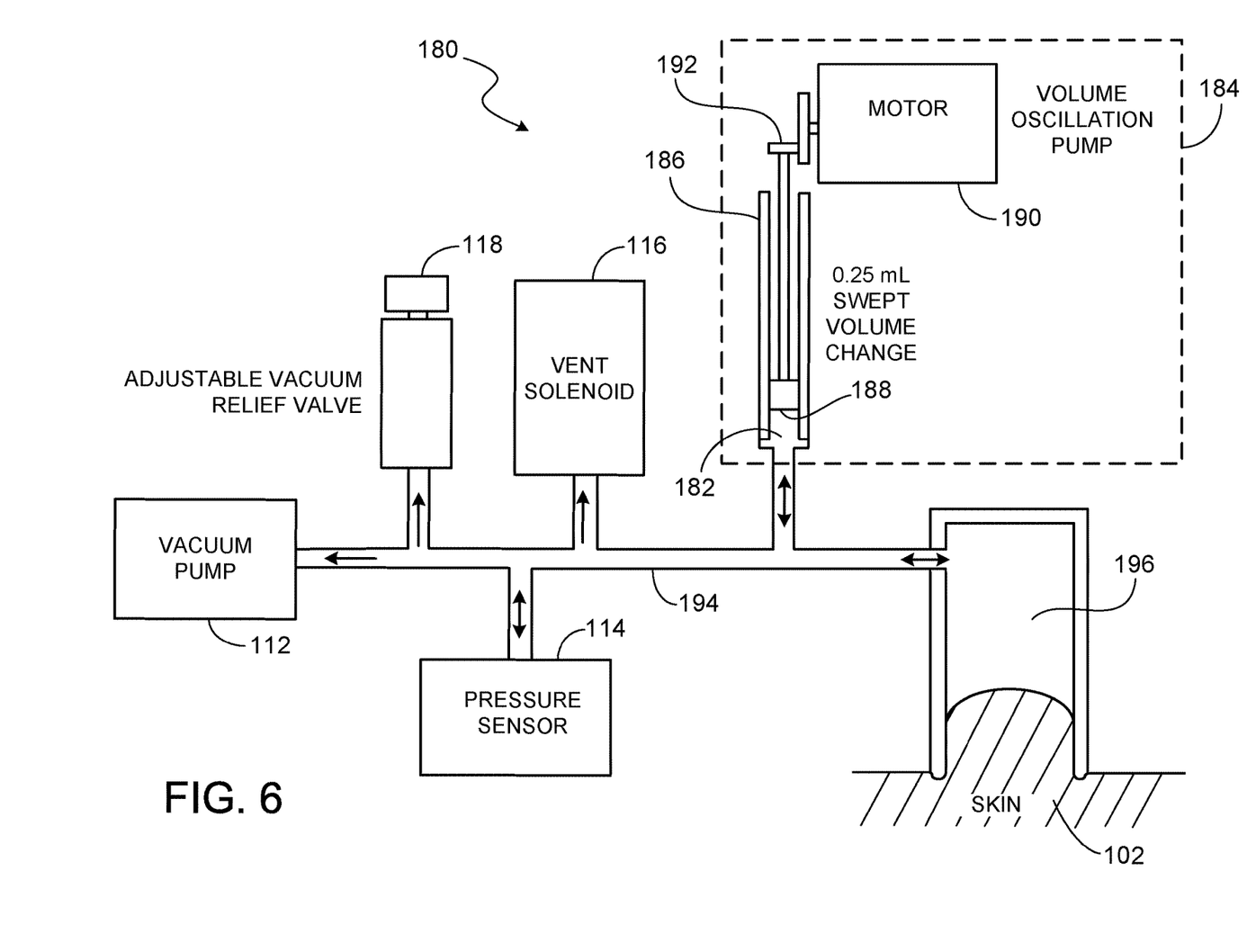
FIG. 6 is a schematic diagram of a skin measuring system.

FIG. 6 is a schematic diagram of an example of a skin measuring system 180 for measuring mechanical properties of a skin 102. The system 180 includes a first chamber 196 (e.g., a cuvette) that covers a portion of the skin 102 to be measured. The system 108 also includes a motorized syringe unit 184 that includes a second chamber 182, e.g., formed by a low friction syringe 186, that is coupled to the first chamber 196 through a tube 194. The syringe 186 has a plunger (piston) 188 that is driven by a small geared motor 190, which provides sufficient torque to drive the syringe plunger 188 in the presence of a substantial vacuum in the second chamber 182. The syringe piston 188 is driven in and out of the second chamber 182 in an oscillating, sinusoidal fashion using an off-axis connection 192 to the motor 190.

The system 180 includes a vacuum pump 112, a pressure sensor 114, a vent solenoid 116, and an adjustable vacuum relief valve 118, similar to those shown in FIG. 1. When the vacuum pump 112 pumps air out of the first chamber 126 and the second chamber 182, the air pressure in the first chamber 196 is reduced and the skin 102 is stretched upwards. This stretching of the skin 102 causes the volume within the first chamber 196 to decrease. In addition, the syringe 186 can generate, e.g., a 0.25 mL volume change in the second chamber 182 by changing the position of the plunger 188. For example, when the plunger 188 is at its highest position, the volume of the second chamber 182 is 0.25 ml greater than when the plunger 182 is at its lowest point.

The small geared motor 190 can be, e.g., a motor available from FischerTechnik, Germany. The syringe 186 can be, e.g., a precision graduated, glass syringe, having a total volume of 2.0 ml.

The system 180 measures skin displacement by measuring changes in the volume of the skin 102 inside the first chamber 196 by measuring changes in the air volume in the first chamber 126. The changes of the air volume in the first chamber 196 is determined by changing the air volume of the second chamber 182 and measuring the changes in air pressure. The motor 190 operates to drive the plunger 188 up and down periodically for a period of time, causing the volume of the second chamber 182 to oscillate with a 0.25 mL volume change. The change in air pressure and the volume occupied by the skin in its stretched state is determined. The system 180 is calibrated such that at different pressures the volume of the skin 102 is measured, resulting in a mapping or relationship between the air pressure and the volume of skin in the first chamber 196. This relationship allows a prediction of the volume of a deformed skin based on the measured pressure in the chamber 196. The change in volume of the skin 102 over time provides information about the elasticity of the skin 102, which can be used as one of the factors in determining general conditions or healthiness of the skin 102, as described above.

Test data for the skin measurement systems described above are disclosed in the Appendix "Research and Development of a Portable Device to Measure Skin Mechanics for Use in Quantifying Human Dehydration," by Nicholas Hunter-Jones and Alexander Isakov Other implementations and applications are also within the scope of the following claims. For example, the model numbers, dimensions, and parameters of the components in the skin measurement systems can be different from those described above.

What is claimed is:

1. An apparatus for measuring a characteristic of a skin, the apparatus comprising:
    a first chamber to be positioned adjacent to a skin, the first chamber defining an opening that exposes the skin to changes in an air pressure in the first chamber, wherein the changes in the air pressure causes a volume of the skin to be drawn into the first chamber;
    a second chamber having an adjustable volume and being coupled to the first chamber, the first and second chambers having a common air pressure;
    a pump to reduce the common air pressure in the first and second chambers;
    a pressure sensor to sense the common air pressure; and
    a data processor to determine a change in the volume of the skin in the first chamber based on measurements of the common air pressure by the pressure sensor.

2. The apparatus of claim 1, wherein the apparatus is configured to make a plurality of measurements of the volume of the skin in the first chamber over a period of time as the volume of the skin in the first chamber changes in response to the changes in the air pressure in the first chamber; and
    output the measurements or a value derived from the measurements.

3. The apparatus of claim 2, wherein the apparatus is further configured to vary a volume of the second chamber that is coupled to the first chamber to cause the common air pressure in both the first and second chambers to vary over the period of time.

4. The apparatus of claim 3 wherein making a plurality of measurements of the volume of the skin in the first chamber comprises making a plurality of measurements of the common air pressure in the first and second chambers over the period of time as the air pressure changes in response to the variations in the volume of the second chamber, and determining the volume of the skin in the first chamber based on the measurements of the common air pressure.

5. The apparatus of claim 3 wherein varying the volume of the second chamber comprises driving a piston or plunger in and out of the second chamber.

6. The apparatus of claim 5 wherein driving the piston or plunger in and out of the second chamber comprises driving the piston or plunger in and out of the second chamber in an oscillating fashion.

7. The apparatus of claim 2 wherein the apparatus is configured to:
    reduce the air pressure in the first chamber to cause the skin to reach a stretched state and enter the first chamber, causing the volume in the first chamber to decrease;
    vary a volume of the second chamber to cause the air pressure in both the first and second chambers to vary;
    wherein making a measurement of the volume of the skin in the first chamber comprises:
    making a first measurement of an air pressure common to the first and second chambers when the second chamber has a first volume;
    making a second measurement of the air pressure in the first and second chambers when the second chamber has a second volume; and
    estimating the volume of the skin in the stretched state in the first chamber based on the first and second measurements of the air pressure in the first and second chambers.

8. The apparatus of claim 2, wherein the apparatus is configured to provide an indication of a likelihood of dehydration of a person or an animal based on the measurements of the volume of the skin in the first chamber or the value derived from the measurements.

9. The apparatus of claim 2, wherein the apparatus is configured to form an air-tight coupling between the skin and a rim surrounding the opening.

10. The apparatus of claim 1 wherein the second chamber comprises a motor and a syringe, the motor to drive a plunger of the syringe to change the volume of the second chamber.

11. The apparatus of claim 10, comprising a controller configured to control the motor to drive the plunger in and out of the second chamber to change the volume of the second chamber.

12. The apparatus of claim 11 wherein the controller is configured to control the motor to drive the plunger in and out of the second chamber in an oscillating fashion.

13. The apparatus of claim 1, comprising a storage device to store information about a mapping between an air pressure in the first chamber and a volume of skin in the first chamber.

14. The apparatus of claim 13 wherein the data processor is configured to estimate the volume of the skin in the first chamber based on the mapping between the air pressure in the first chamber and the volume of skin in the first chamber.

15. The apparatus of claim 1 wherein the apparatus comprises a controller that is configured to:
    cause the pressure sensor to make a first measurement of the air pressure in both the first chamber and the second chamber when the second chamber has a first volume,
    cause the volume of the second chamber to vary from the first volume to a second volume, and cause the pressure sensor to make a second measurement of the air pressure in both the first chamber and the second chamber when the second chamber has the second volume, wherein the data processor is configured to determine the volume of the air in the first chamber based on the first and second measurements of the air pressure.

16. The apparatus of claim 15 wherein the data processor is configured to determine the volume of the skin in the first chamber based on the volume of the air in the first chamber.

17. The apparatus of claim 16 wherein the data processor is configured to provide an indication of a likelihood of dehydration of a person or an animal based on the determined volume of the skin in the first chamber over a period of time or a value derived from the determined volume of the skin in the first chamber over the period of time.

18. The apparatus of claim 1 wherein the apparatus comprises a controller that is configured to, for each of a plurality of measurements of the volume of the skin in the first chamber:

cause the pressure sensor to make a first measurement of the air pressure in both the first chamber and the second chamber when the second chamber has a first volume, cause the volume of the second chamber to vary from the first volume to a second volume, and cause the pressure sensor to make a second measurement of the air pressure in both the first chamber and the second chamber when the second chamber has the second volume, wherein the data processor is configured to determine the volume of air in the first chamber based on the first and second measurements of the air pressure, and determine the volume of the skin in the first chamber based on the volume of the air in the first chamber.

19. The apparatus of claim 1, comprising a vent valve to provide a passage between the chamber at an atmosphere.

20. The apparatus of claim 1, comprising an adjustable vacuum relief valve that is configured to control a level of vacuum in the first and second chambers.

21. The apparatus of claim 1, comprising a tube that is coupled to the first chamber, the second chamber, the pump, and the pressure sensor.

22. The apparatus of claim 21 wherein the tube is also coupled to a vent value and an adjustable vacuum relief valve.

23. A method comprising:

varying an air pressure in a first chamber positioned adjacent to a skin, the first chamber defining an opening that exposes the skin to changes in the air pressure in the first chamber that result in a volume of the skin being drawn into the first chamber;

making a plurality of measurements of the volume of the skin in the first chamber over a period of time as the volume of the skin in the first chamber changes in response to the changes in the air pressure in the first chamber;

outputting the measurements or a value derived from the measurements; and implementing a calibration process that includes varying the air pressure among a plurality of different air pressures to cause a plurality of different volumes of skin to enter the first chamber, and generating a mapping between the plurality of different air pressures and the plurality of different volumes of the skin in the first chamber.

24. The method of claim 23, wherein making the plurality of measurements of the volume of the skin in the first chamber comprises estimating the volume of the skin in the first chamber based on a mapping between the air pressure in the first chamber and the volume of skin in the first chamber.

25. The method of claim 23 wherein making the plurality of measurements of the volume of the skin in the first chamber comprises:

making a first measurement of the common air pressure in both the first chamber and the second chamber when the second chamber has a first volume;

varying the volume of the second chamber from the first volume to a second volume;

making a second measurement of the common air pressure in both the first chamber and the second chamber when the second chamber has the second volume; and determining the volume of the air in the first chamber based on the first and second measurements of the air pressure.

26. The method of claim 25 wherein making the plurality of measurements of the volume of the skin in the first chamber comprises determining the volume of the skin in the first chamber based on the volume of the air in the first chamber.

27. The method of claim 26, further comprising providing an indication of a likelihood of dehydration of a person or an animal based on the measurements of the volume of the skin in the first chamber over the period of time or a value derived from the measurements of the volume of the skin in the first chamber over the period of time.

28. A method comprising:

varying an air pressure in a first chamber positioned adjacent to a skin, the first chamber defining an opening that exposes the skin to changes in the air pressure in the first chamber that result in a volume of the skin being drawn into the first chamber;

making a plurality of measurements of the volume of the skin in the first chamber over a period of time as the volume of the skin in the first chamber changes in response to the changes in the air pressure in the first chamber; and outputting the measurements or a value derived from the measurements; and wherein a second chamber is coupled to the first chamber, and each of the plurality of measurements of the volume of the skin in the first chamber comprises:

making a first measurement of an air pressure common to the first chamber and the second chamber when the second chamber has a first volume;

varying the volume of the second chamber from the first volume to a second volume;

making a second measurement of the air pressure in both the first chamber and the second chamber when the second chamber has the second volume;

determining the volume of air in the first chamber based on the first and second measurements of the air pressure; and determining the volume of the skin in the first chamber based on the volume of the air in the first chamber.

29. The method of claim 28, further comprising providing an indication of a likelihood of dehydration of a person or an animal based on the measurements of the volume of the skin in the first chamber over the period of time or a value derived from the measurements of the volume of the skin in the first chamber over the period of time.

30. A method comprising:

varying an air pressure in a first chamber positioned adjacent to a skin, the first chamber defining an opening that exposes the skin to changes in the air pressure in the first chamber that result in a volume of the skin being drawn into the first chamber;

making a plurality of measurements of the volume of the skin in the first chamber over a period of time as the volume of the skin in the first chamber changes in response to the changes in the air pressure in the first chamber;

outputting the measurements or a value derived from the measurements;

wherein a second chamber is coupled to the first chamber, and the method comprises:

reducing the air pressure in the first chamber to cause the skin to reach a stretched state and enter the first chamber, causing the volume in the first chamber to decrease;

varying a volume of the second chamber to cause an air pressure common to both the first and second chambers to vary;

making a first measurement of the air pressure common to the first and second chambers when the second chamber has a first volume;

making a second measurement of the air pressure common to the first and second chambers when the second chamber has a second volume;

estimating the volume of the skin in the stretched state in the first chamber based on the first and second measurements of the air pressure common to the first and second chambers;

wherein the method comprises returning the pressure common to the first and second chamber to atmospheric pressure; and during a period of time that the skin changes from the stretched state to a normal state, varying the volume of the second chamber to cause the air pressure common to the first and second chambers to vary over the period of time, measuring the air pressure common to the first and second chambers during the period of time, and estimating changes in the volume of the skin in the first chamber over the period of time based on the measurements of the air pressure common to the first and second chambers during the period of time.

31. The method of claim 30, further comprising providing an indication of a likelihood of dehydration of a person or an animal based on the estimated changes in the volume of the skin in the first chamber over the period of time or a value derived from the estimated changes in the volume of the skin in the first chamber over the period of time.

* * * * *

UNITED STATES PATENT AND TRADEMARK OFFICE
CERTIFICATE OF CORRECTION

| | |
|---|---|
| PATENT NO. | : 11,259,741 B2 |
| APPLICATION NO. | : 16/026813 |
| DATED | : March 1, 2022 |
| INVENTOR(S) | : Nicholas Hunter-Jones and Alexander Isakov |

It is certified that error appears in the above-identified patent and that said Letters Patent is hereby corrected as shown below:

In the Specification

Column 1, Line 8, delete "Apr. 8" and insert -- Apr. 18 --.

Signed and Sealed this
Twenty-first Day of June, 2022

Katherine Kelly Vidal
*Director of the United States Patent and Trademark Office*